US012593972B2

(12) United States Patent
Suresh et al.

(10) Patent No.: US 12,593,972 B2
(45) Date of Patent: Apr. 7, 2026

(54) INTEGRATED ANALYSIS OF MULTIPLE SPECTRAL INFORMATION FOR OPHTHALMOLOGY APPLICATIONS

(71) Applicant: Alcon Inc., Fribourg (CH)

(72) Inventors: Vignesh Suresh, Woodland Hills, CA (US); Shruti Siva Kumar, Foothill Ranch, CA (US); Lu Yin, Keller, TX (US); Ramesh Sarangapani, Coppell, TX (US)

(73) Assignee: Alcon Inc., Fribourg (CH)

( * ) Notice: Subject to any disclaimer, the term of this patent is extended or adjusted under 35 U.S.C. 154(b) by 336 days.

(21) Appl. No.: 18/358,881

(22) Filed: Jul. 25, 2023

(65) Prior Publication Data

US 2024/0032784 A1 Feb. 1, 2024

Related U.S. Application Data

(60) Provisional application No. 63/394,156, filed on Aug. 1, 2022.

(51) Int. Cl.
| | |
|---|---|
| *A61B 3/00* | (2006.01) |
| *A61B 3/14* | (2006.01) |
| *G16H 50/30* | (2018.01) |

(52) U.S. Cl.
CPC .............. *A61B 3/0025* (2013.01); *A61B 3/14* (2013.01); *G16H 50/30* (2018.01)

(58) Field of Classification Search
CPC .. G01J 3/2823; G01J 3/10; G01J 3/433; G01J 2003/102; G01J 2003/2826; G01J 2003/4334; A61B 3/14; A61B 3/10
(Continued)

(56) References Cited

U.S. PATENT DOCUMENTS

| | | | |
|---|---|---|---|
| 7,246,905 | B2 | 7/2007 | Benedikt |
| 9,185,357 | B2 | 11/2015 | Boccara |

(Continued)

FOREIGN PATENT DOCUMENTS

| | | |
|---|---|---|
| CN | 112816420 A | 5/2021 |
| WO | 9916353 A1 | 4/1999 |

(Continued)

OTHER PUBLICATIONS

Ayon Dey, Machine learning algorithms: a review, International jurnal of computer science and information technologies, vol. 7, pp. 1174-1179, 2016.

(Continued)

*Primary Examiner* — Mohammed A Hasan

(57) ABSTRACT

In certain embodiments, an ophthalmic system and computer-implemented method for analyzing multiple spectral information to generate ophthalmic information are described. In an exemplary ophthalmic system, multiple spectral information associated with an eye of a patient is captured via an imaging system. A first set of information and a second set of information are extracted from the multiple spectral information. A visualization of the multiple spectral information is generated using the first set of information. The first set of information and the second set of information are evaluated using different deep learning models to generate ophthalmic information. The ophthalmic information is sent to a user for diagnostic evaluation.

18 Claims, 9 Drawing Sheets

(58) Field of Classification Search
USPC .......................................................... 351/200
See application file for complete search history.

(56) References Cited

U.S. PATENT DOCUMENTS

| | | |
|---|---|---|
| 2004/0085542 A1 | 5/2004 | Soliz et al. |
| 2006/0140497 A1 | 6/2006 | Kondo et al. |
| 2007/0156021 A1 | 7/2007 | Morse et al. |
| 2010/0085537 A1 | 4/2010 | Ramella-roman et al. |
| 2012/0065518 A1 | 3/2012 | Mangoubi |
| 2013/0128227 A1 | 5/2013 | Cui et al. |
| 2014/0002793 A1 | 1/2014 | Hogan |
| 2014/0276025 A1 | 9/2014 | Durbin |
| 2014/0300864 A1 | 10/2014 | Fukuma |
| 2015/0015692 A1 | 1/2015 | Smart |
| 2016/0278678 A1 | 9/2016 | Valdes et al. |
| 2016/0338588 A1 | 11/2016 | Friedman |
| 2016/0360958 A1* | 12/2016 | Tsuri ..................... A61B 3/0025 |
| 2017/0042464 A1 | 2/2017 | Verdooner |
| 2017/0059408 A1 | 3/2017 | Krner et al. |
| 2017/0176336 A1 | 6/2017 | Dimitriadis et al. |
| 2017/0297144 A1 | 10/2017 | Nakanishi |
| 2018/0136486 A1* | 5/2018 | Macnamara ............. A61B 3/00 |
| 2019/0298170 A1 | 10/2019 | Artal Soriano et al. |
| 2019/0343384 A1 | 11/2019 | Plaian |
| 2021/0169324 A1 | 6/2021 | Tripathi et al. |
| 2022/0151568 A1 | 5/2022 | Yao |
| 2022/0157470 A1 | 5/2022 | Sylvestre |
| 2022/0160228 A1 | 5/2022 | Leahy et al. |
| 2022/0225877 A1* | 7/2022 | Shiba ..................... A61B 3/102 |
| 2022/0240779 A1 | 8/2022 | Peyman |
| 2022/0260413 A1 | 8/2022 | Perruchot et al. |
| 2023/0018494 A1* | 1/2023 | Gribble ................ A61B 3/0008 |
| 2024/0415383 A1* | 12/2024 | Shaked .................. G02B 27/62 |
| 2025/0150564 A1* | 5/2025 | Mizutani ................ H04N 25/78 |

FOREIGN PATENT DOCUMENTS

| | | | |
|---|---|---|---|
| WO | 2015023990 A1 | 2/2015 | |
| WO | 2020047594 A1 | 3/2020 | |
| WO | WO-2021151046 A1 * | 7/2021 | ........... A61B 5/4076 |
| WO | 2022011420 A1 | 1/2022 | |
| WO | 2022153320 A1 | 7/2022 | |

OTHER PUBLICATIONS

Chen Qingyu et al., Multi-modal, multi-task, multi-attention (M3) deep learning detection of regular pseudodrusen: towards automated accessible classification of age-related macular degeneration, pp. 1-31, 2020URL: https://arxiv.org/abs/2011.05142vl.

Citation: M. Arsalan et al., Segmenting Retinal Vessels Using a Shallow Segmentation Network to Aid Ophthalmic Analysis, Mathematics, vol. 10, p. 1536, 2022.

J. Fhima et al., PVBM: A Python Vasculature Biomarker Toolbox Based on Retinal Blood Vessel Segmentation, Cornell University, 2022.

Sarraf David et al., Retinal pigment epithelial tears in the era of intravitreal pharmacotherapy: risk factors, pathogenesis, prognosis and treatment (an American Ophthalmological Society thesis), American Ophthalmological Society, Transactions, vol. 112, pp. 142-159, 2014.

Yonlong He, et al., Segmenting Diabetic Retinopathy Lesions in Multispecial Images Using Low-Dimensional Spatial-Spectral Matrix Representation, Ieee Juournal of Biomedical and helth informatics, Ieee, Piscataway, NJ, USA, vol. 24, No. 2, pp. 493-502, Apr. 20, 2019.

Yoon Jonghee, @Hyperspectrial Imaging for Clinical Applications@ Biochip Journal, Korean Biochip, Seoul, South Korea, vol. 16, No. 1, Jan. 4, 2022, pp. 1-12.

William R. Johnson, Snapshot hyperspectral imaging in ophthalmology, Journal of Biomedical Optics, 12 (1), 014036_Jan. 7, 2007.

* cited by examiner

500

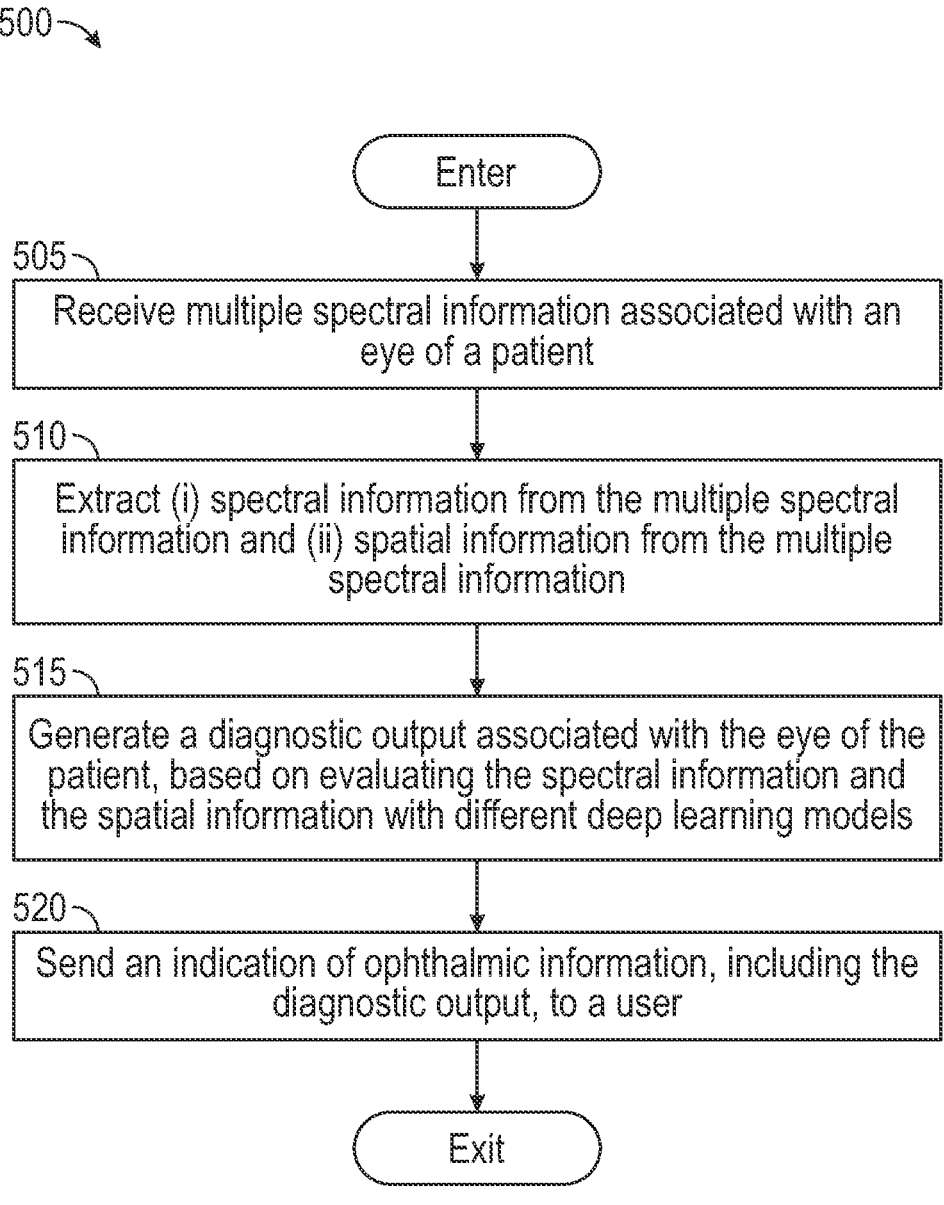

Enter

505
Receive multiple spectral information associated with an eye of a patient

510
Extract (i) spectral information from the multiple spectral information and (ii) spatial information from the multiple spectral information 515
Generate a diagnostic output associated with the eye of the patient, based on evaluating the spectral information and the spatial information with different deep learning models 520
Send an indication of ophthalmic information, including the diagnostic output, to a user Exit

FIG. 5

INTEGRATED ANALYSIS OF MULTIPLE SPECTRAL INFORMATION FOR OPHTHALMOLOGY APPLICATIONS

BACKGROUND

Multispectral imaging (MSI) and hyperspectral imaging (HSI) technologies are increasingly being used for a variety of applications, including, for example, ophthalmology applications. In the ophthalmology domain, MSI and HSI represent non-invasive optical imaging modalities that utilize multiple narrow spectral bands of light to image ocular structures (e.g., cornea, retina, Meibomian gland, etc.). The difference between MSI and HSI generally revolves around the number of bands and how narrow the bands are. MSI, for example, generally involves a smaller number of wider bands, compared to HSI. HSI, in contrast, generally involves a larger number of narrower bands, compared to MSI. Currently, however, there are limitations associated with using MSI/HSI data for ophthalmology applications, including, for example, ocular disease detection. For example, because MSI/HSI data is complex, it is not easy to interpret such data for performing disease diagnosis.

SUMMARY

In certain embodiments, an ophthalmic system is provided. The ophthalmic system includes an imaging system, a memory comprising executable instructions, and a processor in data communication with the memory. The processor is configured to execute the executable instructions to extract a first set of information from the multiple spectral information and a second set of information from the multiple spectral information. The first set of information includes spectral information and the second set of information includes spatial information. The processor is also configured to execute the executable instructions to generate a set of ophthalmic information associated with the eye of the patient, based on evaluating the first set of information with a first deep learning model and the second set of information with a second deep learning model. The processor is further configured to execute the executable instructions to present an indication of the set of ophthalmic information to a user.

In certain embodiments, a computer-implemented method is provided. The computer-implemented method includes receiving multiple spectral information associated with an eye of a patient. The computer-implemented method also includes extracting a first set of information from the multiple spectral information and a second set of information from the multiple spectral information. The first set of information includes spectral information and the second set of information includes spatial information. The computer-implemented method also includes generating a set of ophthalmic information associated with the eye of the patient, based on evaluating the first set of information with a first deep learning model and the second set of information with a second deep learning model. The computer-implemented method further includes presenting an indication of the set of ophthalmic information to a user.

In certain embodiments, a non-transitory computer-readable medium is provided. The non-transitory computer-readable medium has computer executable instructions stored thereon. The computer executable instructions are executable by one or more processors to perform an operation. The operation includes receiving multiple spectral information associated with an eye of a patient. The operation also includes extracting a first set of information from the multiple spectral information and a second set of information from the multiple spectral information. The first set of information includes spectral information and the second set of information includes spatial information. The operation also includes generating a set of ophthalmic information associated with the eye of the patient, based on evaluating the first set of information with a first deep learning model and the second set of information with a second deep learning model. The operation further includes presenting an indication of the set of ophthalmic information to a user.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 5 is a flowchart of a method for analyzing multiple spectral information to generate ophthalmic information, according to certain embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
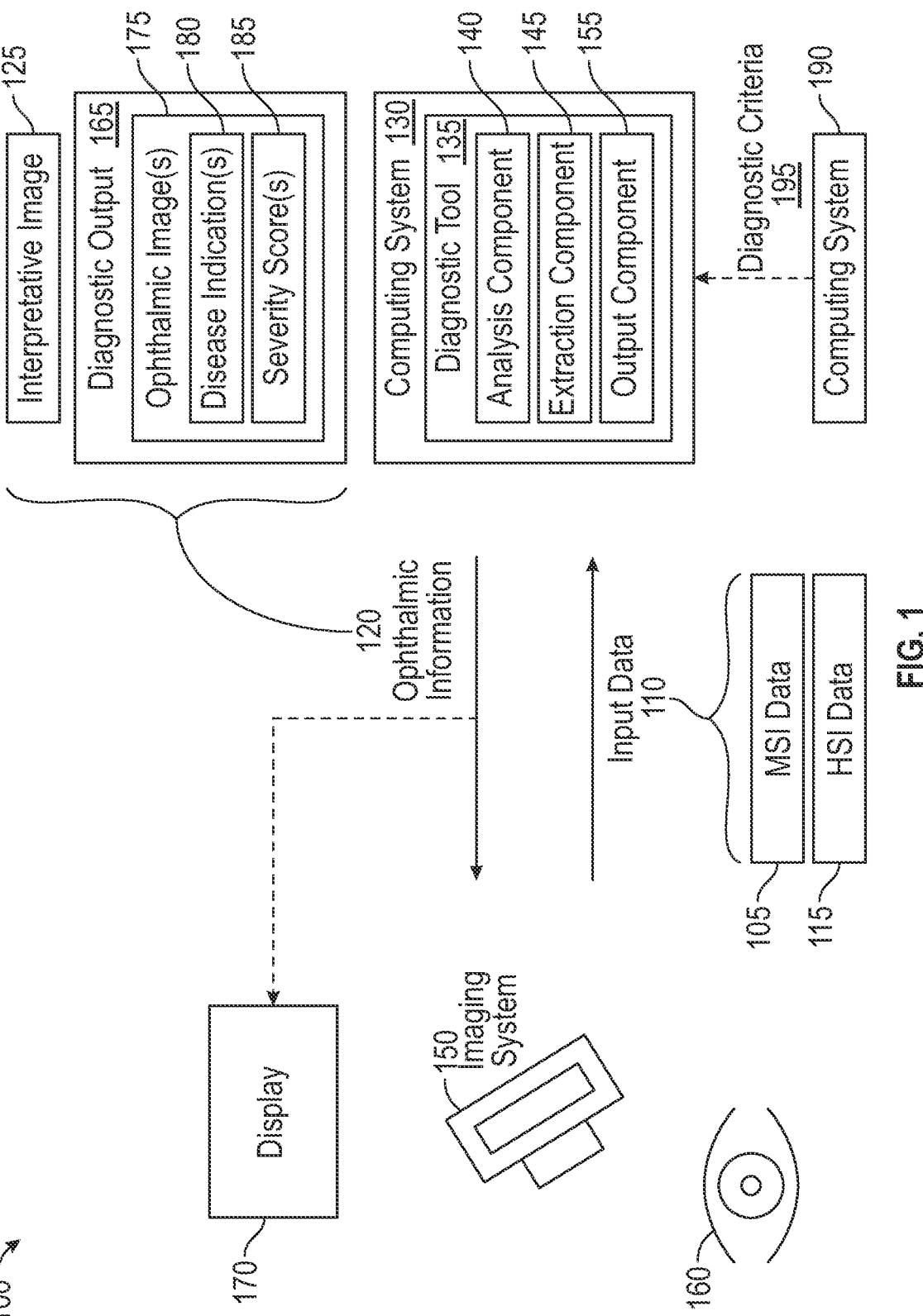
FIG. 1 illustrates an example ophthalmic system for analyzing multiple spectral information to generate ophthalmic information, according to certain embodiments.

In an exemplary ophthalmology field, such as retinal imaging, MSI/HSI can provide a sequence of enface fundus spectral slices, allowing clinicians to visualize both spatial and spectral characteristics of structures throughout the thickness of the retina. Clinicians can use the MSI/HSI data to characterize subtle, deep, or overlapping lesions from the spectral bands, enabling the diagnosis of ocular diseases beyond that which is possible using solely human vision.

Currently, however, MSI/HSI-based diagnosis remains subjective and significantly time consuming due, in part, to reliance on manual estimation of MSI/HSI data by clinicians (e.g., ophthalmology specialists, such as ophthalmologists). For example, current disease diagnosis methods generally rely on clinicians to extensively assess pathological features across the spectral bands and compare these features over multiple spatial locations. However, given that an MSI/HSI sequence may consist of several spectral bands, interpretation of pathology with such a large number of spectral bands is highly complex, making disease diagnosis cumbersome, unreliable, and error-prone. Accordingly, what is needed are improved systems, devices, and techniques for analyzing MSI/HSI data for ophthalmology applications, such as ocular disease detection, for example.

Certain embodiments described herein provide systems, techniques, and devices for analyzing and interpreting MSI/HSI information (or data) for ophthalmology applications, such as disease detection and diagnosis, disease prediction, etc. More specifically, certain embodiments described below provide a framework for applying image analytics and artificial intelligence (AI)/machine learning (ML) to automatically process and present clinically relevant information from data acquired using MSI/HSI technology. In certain embodiments, the framework involves processing the spectral and spatial information in MSI/HSI information separately in order to determine meaningful features that can be used for various purposes, such as disease diagnosis, etc. By processing the spectral and spatial information separately, certain embodiments overcome challenges in interpreting, visualizing, and utilizing MSI/HSI information.

As used herein, the terms "information" and "data" may be used interchangeably to refer to qualitative observations and/or quantitative data. Additionally, as used herein, the term "multiple spectral information" may be used to refer to MSI information and/or HSI information. Further, as used herein, a hyphenated form of a reference numeral refers to a specific instance of an element and the un-hyphenated form of the reference numeral refers to the collective element. Thus, for example, device "12-1" refers to an instance of a device class, which may be referred to collectively as devices "12" and any one of which may be referred to generically as a device "12".

FIG. 1 illustrates an example ophthalmic system 100 for analyzing multiple spectral information (e.g., MSI/HSI information), according to certain embodiments. The ophthalmic system 100 includes an imaging system 150, a computing system 130, a computing system 190, and a display 170. The computing systems 130 and 190 are representative of a variety of computing systems (or devices), including, for example, a laptop computer, mobile computer (e.g., a tablet or a smartphone), a server computer, a desktop computer, an imaging system, a surgical console, a visualization system, a system embedded in a medical device, etc.

The imaging system 150 is representative of an imaging system that can capture multiple spectral information associated with a target (e.g., tissues/structures of the eye 160). The imaging system 150 can include one or more devices/components, such as one or more imaging devices, imaging optics, illumination sources, etc. The imaging devices can include digital cameras, microscopes, or other imaging devices, now known or later developed. In an exemplary embodiment, the imaging device(s) includes a multispectral imaging device (e.g., multispectral camera), a hyperspectral imaging device (e.g., a hyperspectral camera), or a combination thereof. The imaging system 150 can employ a variety of different imaging modalities to obtain multiple spectral information. For example, the imaging system 150 can obtain multiple spectral information based on reflectance light, polarized light, and other light properties.

The computing system 130 includes a diagnostic tool 135, which is generally configured to perform one or more techniques described herein for analyzing multiple spectral information for ophthalmology applications. The diagnostic tool 135 includes an analysis component 140, an extraction component 145, and an output component 155, each of which can include hardware components, software components, or combinations thereof. In certain embodiments, the diagnostic tool 135 receives input data 110 from the imaging system 150 and generates ophthalmic information 120, based on an evaluation of the input data 110 using techniques described herein. The input data 110 generally includes multiple spectral information. In certain embodiments, the multiple spectral information includes MSI data 105. In certain embodiments, the multiple spectral information includes HSI data 115.

Compared to MSI data 105, HSI data 115 generally includes a larger number of narrower spectral bands. An exemplary HSI data configuration can include, for example, hundreds of spectral bands in the range of 10-20 nanometers (nm). On the other hand, compared to HSI data 115, MSI data 105 generally includes a smaller number of wider spectral bands. An exemplary MSI data configuration can include, for example, tens of spectral bands generally in the range of 20 nm and above.

In certain embodiments, the diagnostic tool 135 separates the input data 110 into spectral components and spatial components, and analyzes the spectral and spatial components separately using one or more of the analysis component 140, extraction component 145, and output component 155, in order to generate the ophthalmic information 120. Note that the analysis component 140, extraction component 145, and output component 155 are described in greater detail below.

In certain embodiments, the diagnostic tool 135 receives diagnostic criteria 195 (also referred to as diagnostic information) from a computing system 190. The computing system 190 may enable a user (e.g., clinician, such as an ophthalmologist) to interact with the diagnostic tool 135 in generating ophthalmic information 120. For example, the diagnostic criteria 195 is generally representative of input from the user regarding the input data 110. For instance, the user may indicate to the diagnostic tool 135 particular spectral bands to focus on, certain diseases to generate a prediction for, and so on. In certain embodiments, the diagnostic tool 135 generates the ophthalmic information 120 based on the diagnostic criteria 195 and the input data 110.

The ophthalmic information 120 includes an interpretative image 125 and a diagnostic output 165. The interpretative image 125 may be an interpretative MSI image or an interpretative HSI image. In general, the interpretative image 125 is a multiple spectral image that is more easily interpretable by a user (e.g., clinician) compared to a multiple spectral image in the input data 110. For example, the interpretive image 125 may include various retinal features present in different spectral bands that are superimposed on a single frame. Presenting the retinal features in such a manner (e.g., on a single frame) may aid the user in interpreting, visualizing, and/or utilizing the multiple spectral information (e.g., retinal features across the spectral bands) in a more effective and/or easier manner when making a disease diagnosis.

The diagnostic output 165 may include information associated with a prediction of at least one disease of the patient's eye 160, based on an analysis of the input data 110. As shown, the diagnostic output 165 includes or is provided as one or more ophthalmic images 175. Each of the one or more ophthalmic images 175 may have one or more disease indications 180 and one or more severity scores 185 corresponding to the one or more disease indications 180. For example, an ophthalmic image 175 may have a disease indication 180 overlaid onto the ophthalmic image 175 and an indication of the corresponding severity score 185 overlaid onto the ophthalmic image 175.

In certain embodiments, the disease indication(s) 180 is a segmented region(s) of the respective ophthalmic image 175 that is associated with a particular ocular disease (e.g., retinal disease). In certain embodiments, the severity score 185 includes (i) an indication (or prediction) of an ocular disease for the disease indication 180 (e.g., segmented region) within the ophthalmic image 175 and (ii) an indication of the severity of the ocular disease. In an exemplary embodiment, the severity score 185 includes a ranking. The ranking may be based on a predefined scale (e.g., 0 to 10, 0 to 100), where one end of the scale is associated with a lowest severity and the other end of the scale is associated with a highest severity. In another exemplary embodiment, the severity score 185 includes a confidence score (e.g., an indication of the likelihood that the disease prediction is correct). The confidence score may be a percentage. Note, however, that these are merely examples of forms that the severity score(s) 185 may have and that the severity score(s) 185 may have any form/configuration consistent with the functionality described herein.

In an exemplary diagnostic output 165, a first ophthalmic image 175-1 may have a first disease indication 180-1 of a first retinal disease (e.g., one or more segmented regions in the first ophthalmic image 175-1 that indicate the first retinal disease) and a severity score 185-1 for the first retinal disease based on the first disease indication 180-1; a second ophthalmic image 175-2 may have a second disease indication 180-2 of a second retinal disease (e.g., one or more segmented regions in the second ophthalmic image 175-2 that indicate the second retinal disease) and a severity score 185-2 for the second retinal disease based on the second disease indication 180-2; and so on.

The ophthalmic information 120 (including the interpretative image 125 and the diagnostic output 165) is made available to a user (e.g., a clinician, such as an ophthalmologist), which can use the ophthalmic information 120 to make a disease diagnosis for the patient. In certain embodiments, the ophthalmic information 120 is transmitted to the imaging system 150 for display via the imaging system 150. For example, at least a portion of the ophthalmic information 120 may be presented in the field-of-view (FOV) of the imaging system 150 as an overlay, using augmented reality or other display technology. Additionally or alternatively, in certain embodiments, the ophthalmic information 120 is transmitted to a display 170, which is capable of displaying to a user (e.g., ophthalmologist) ophthalmic information 120 associated with the eye 160.

In the illustrated embodiment, display 170 is separate from imaging system 150 and the computing system 130. In some other embodiments, display 170 is integral with imaging system 150 or with computing system 130. In yet other embodiments, the imaging system 150, computing system 130, and the computing system 190 are implemented as a single computing system. In certain embodiments, display 170 includes an augmented reality display. In certain embodiments, display 170 includes a virtual reality display. In certain embodiments, display 170 includes a three-dimensional display.

Note that FIG. 1 illustrates a reference example of an ophthalmic system for analyzing multiple spectral information and that, in other embodiments, the ophthalmic system may have different configurations. For example, while FIG. 1 depicts computing system 130, imaging system 150, computing system 190, and display 170 as separate components, in certain embodiments, the computing system 130, imaging system 150, computing system 190, and display 170 may be a part of a single computing system (or device) that analyzes multiple spectral information, generates ophthalmic information, and presents the ophthalmic information to the user. In general, the ophthalmic system may be implemented using any number of components (e.g., greater or fewer number of components than what is illustrated in FIG. 1).

Figure 2A:
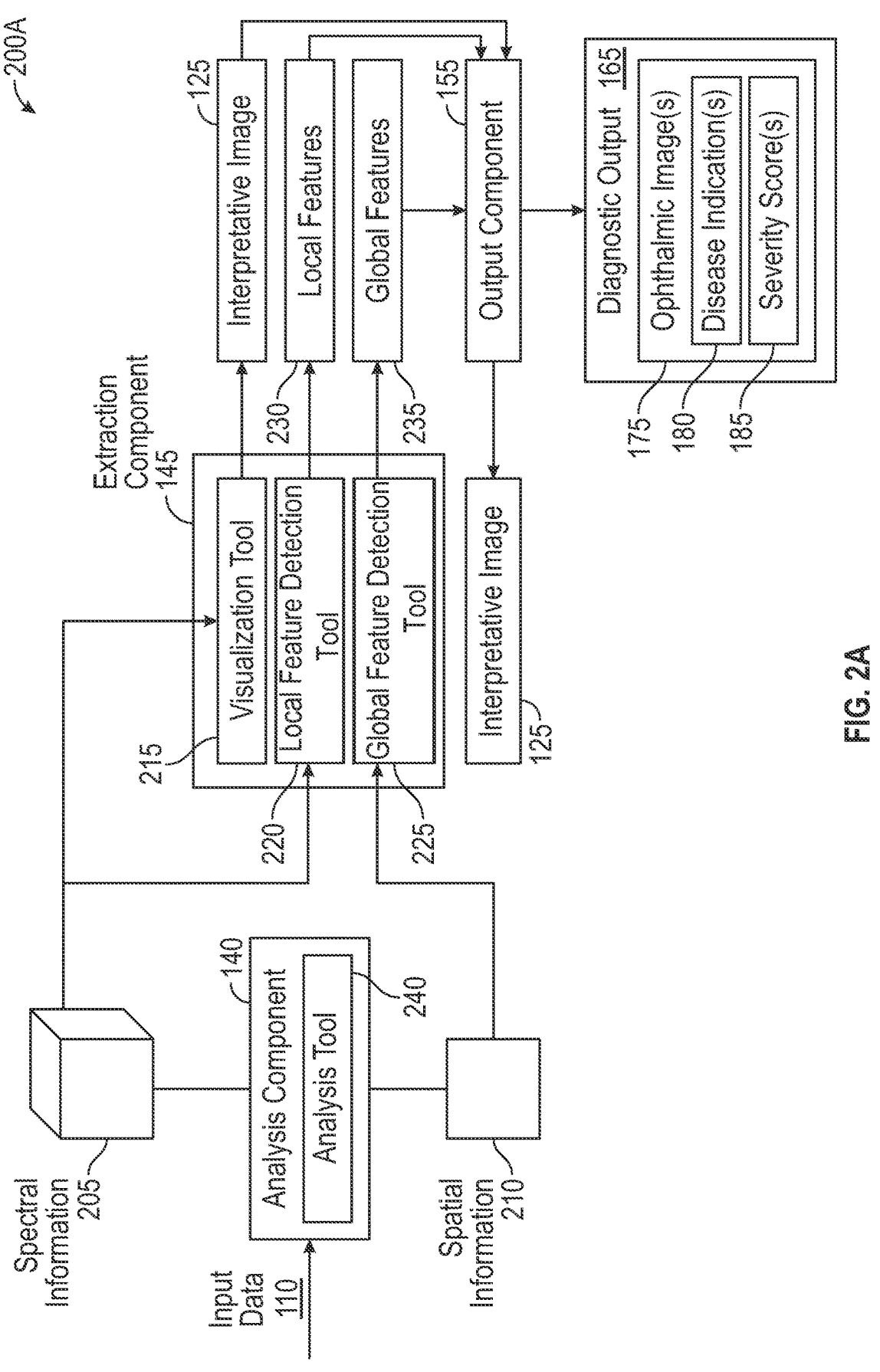
FIG. 2A illustrates an example workflow for analyzing multiple spectral information to generate ophthalmic information, according to certain embodiments.

FIG. 2A illustrates an example workflow 200A for analyzing multiple spectral information to generate ophthalmic information, according to certain embodiments. The workflow 200A may be performed by the diagnostic tool 135.

In certain embodiments, the analysis component 140 includes an analysis tool 240, which is generally configured to separate (or decouple) multiple spectral information into spectral components and spatial components. As shown in FIG. 2A, for example, the analysis tool 240 receives input data 110 and extracts spectral information 205 and spatial information 210 from the input data 110. The analysis component 140 sends the spectral information 205 and spatial information 210 to the extraction component 145.

The spectral information 205 generally represents the raw multiple spectral information sequence (e.g., raw MSI sequence or raw HSI sequence). For example, the spectral information 205 is generally multidimensional and includes information from across multiple spectral bands. In contrast, the spatial information 210 is generally one-dimensional and may include spatial characteristics of the eye (e.g., position (including location and/or orientation) of certain features of the eye).

In certain embodiments, the analysis tool 240 performs dimensionality reduction on the input data 110 in order to extract the spatial information 210. An exemplary dimensionality reduction technique (or method) is principal component analysis (PCA). Note, however, that PCA is an example and that any dimensionality reduction techniques consistent with the functionality described herein can be used.

In certain embodiments, the extraction component 145 includes a visualization tool 215, a local feature detection tool 220, and a global feature detection tool 225. The visualization tool 215 is configured to generate the interpretative image 125 based on the spectral information 205. As noted, the interpretative image 125 is a multiple spectral image that is more easily interpretable (by a user) compared to a multiple spectral image in the input data 110. For example, the interpretative image 125 may be a single image, which includes one or more superimposed features (from across one or more spectral bands) from the spectral information 205. The visualization tool 215 may employ deterministic techniques (e.g., weighted averaging) or learning-based techniques (e.g., convolutional neural networks (CNNs), recurrent neural networks (RNNs), etc.) to extract the features from the spectral information 205 and superimpose the amalgamated features on the single interpretative image 125. Note that the visualization tool 215 is described in greater detail below with respect to FIG. 3.

In certain embodiments, the extraction component 145 processes the spectral information 205 and the spatial information 210 separately using the local feature detection tool 220 and the global feature detection tool 225, respectively. For example, the local feature detection tool 220 is generally configured to perform local feature detection based on the spectral information 205, and the global feature detection tool 225 is generally configured to perform global feature detection based on the spatial information 210. The local feature detection tool 220 and the global feature detection tool 225 may use one or more deep learning techniques (or models) (e.g., 2D CNN, 3D CNN, autoencoder, etc.) to perform the respective local feature detection and global feature detection.

In certain embodiments, the local feature detection tool 220 performs local feature detection by extracting local features 230 from the spectral information 205. The local feature(s) 230 may correspond to one or more diseased regions of an eye. As used herein, a local feature 230 may refer to a spectral feature extracted from a local area (e.g., single image pixel) of a spectral image within the spectral information 205. In certain embodiments, the global feature detection tool 225 performs global feature detection by extracting global features 235 from the spatial information 210. Similar to the local feature(s) 230, the global features 235 may also correspond to one or more diseased regions of an eye. As used herein, a global feature 235 may refer to a spatial extent feature extracted from a spatial image within the spatial information 210. Note, the local feature detection tool 220 and the global feature detection tool 225 are described in greater detail below with respect to FIG. 4.

The output component 155 receives the local features 230 and the global features 235 and generates a diagnostic output 165. In certain embodiments, the output component 155 concatenates the local features 230 and global features 235 to obtain at least one ophthalmic image 175 with one or more disease indications 180. For example, the at least one ophthalmic image 175 may be a retinal image, and the one or more disease indications 180 may include one or more segmented disease regions within the retinal image. The output component 155 may also provide (as part of the diagnostic output 165) a severity score 185 associated with the disease indications 180. For example, the severity score 185 may indicate a particular retinal disease associated with the segmented disease regions along with a score indicating a severity of the retinal disease. In addition to or as an alternative to the diagnostic output 165, the output component 155 may provide the interpretative image 125 (received from the visualization tool 215) to a user (e.g., via imaging system 150 and/or display 170). As noted above, the interpretative image 125 is a single image having with one or more features from different spectral bands superimposed on the single image. The interpretative image 125 may enable the user to interpret the multiple spectral information obtained from the imaging system 150 in a more effective and/or easier manner when making a disease diagnosis. Note that the output component 155 is described in greater detail below with respect to FIG. 4.

Figure 2B:
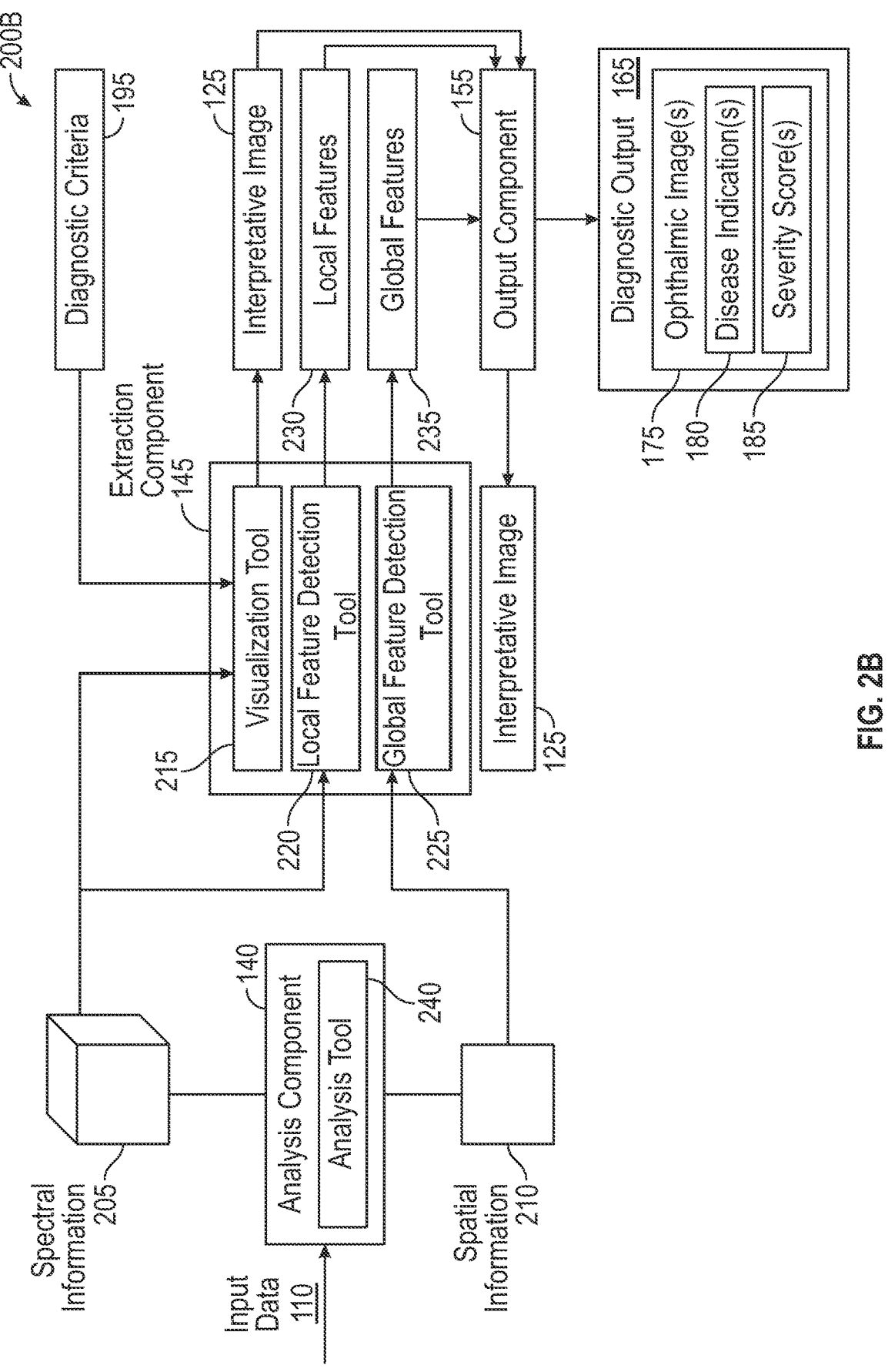
FIG. 2B illustrates another example workflow for analyzing multiple spectral information to generate ophthalmic information, according to certain embodiments.

FIG. 2B illustrates another example workflow 200B for analyzing multiple spectral information to generate ophthalmic information, according to certain embodiments. The workflow 200B may be performed by the diagnostic tool 135. Compared to the workflow 200A depicted in FIG. 2A, in the workflow 200B, the visualization tool 215 of the extraction component 145 receives diagnostic criteria 195 as an additional input to the spectral information 205. In certain embodiments, a user (e.g., clinician) may interact with the diagnostic tool 135 via the diagnostic criteria 195. For example, the user may indicate within the diagnostic criteria 195 one or more spectral bands of interest, one or more ocular features of interest, one or more ocular diseases, etc. The visualization tool 215 may use the diagnostic criteria 195 to generate a custom (or user-defined) interpretative image 125. For example, the visualization tool 215 may filter the amount of spectral features that are superimposed onto the interpretative image 125 according to the diagnostic criteria 195. One benefit of filtering spectral features in this manner is that the user can be shown a single image that focuses on particular spectral features, allowing the user to use such features in a more effective and/or easier manner when making a disease diagnosis.

Note that FIGS. 2A-2B illustrate reference example configurations of workflows 200A and 200B, respectively, that can be used to analyze multiple spectral information to generate ophthalmic information and that the workflows 200A and 200B may have other configurations consistent with the functionality described herein. For example, while the workflows 200A and 200B are described as being implemented with a visualization tool 215, a local feature detection tool 220, and a global feature detection tool 225, each of the workflows 200A and 200B may be implemented using any number of components (e.g., a single component, multiple components, etc.).

Figure 3:
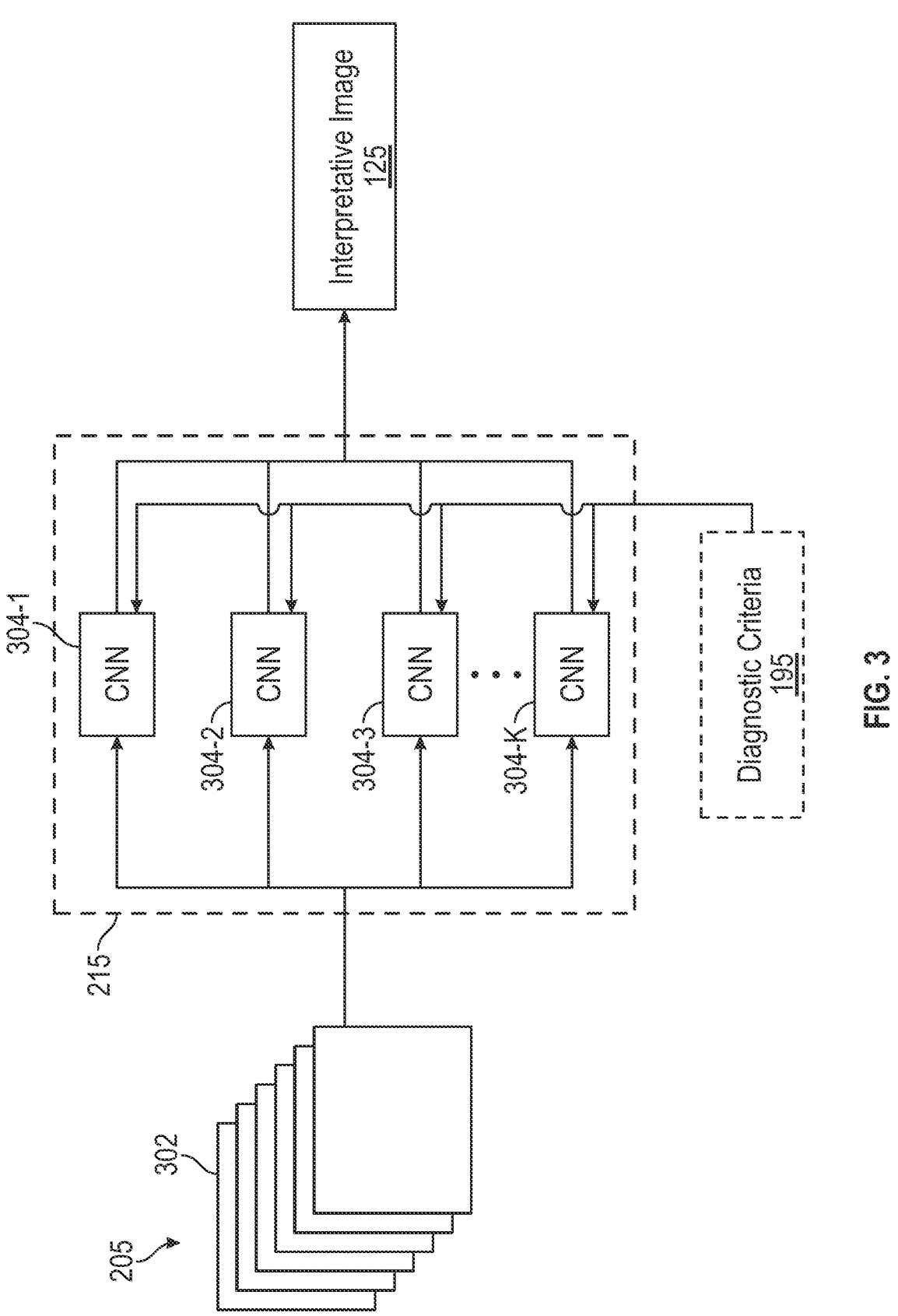
FIG. 3 further illustrates certain components of the workflows illustrated in FIGS. 2A-2B, according to certain embodiments.

FIG. 3 further illustrates certain components of the visualization tool 215, described relative to FIGS. 2A-2B, according to certain embodiments. As shown, the visualization tool 215 includes CNNs 304 1-K, which are generally configured to process the spectral information 205 in order to generate the interpretative image 125. In an exemplary embodiment, the spectral information 205 includes different spectral bands 302 (also referred to as spectral frames) of a multiple spectral image (e.g., MSI image or HSI image). In such an embodiment, the visualization tool 215 can extract features from one or more of the spectral bands and superimpose the features on a single interpretative image 125.

As also shown in FIG. 3, in certain embodiments, the CNNs 304 1-K may receive diagnostic criteria 195 as an input. As noted, a user may use the diagnostic criteria 195 to configure the type of output to examine for diagnosis. For example, the interpretative image 125 may be a custom (or user-defined) image with a set of features (from across the spectral bands 302) selected (or configured) by the user.

Note that while FIG. 3 depicts the visualization tool 215 implementing a learning based technique with one or more CNNs to process the spectral information 205, in certain embodiments, the visualization tool 215 can use other techniques, including, for example, deterministic methods (e.g., weighted averaging) or learning based methods (e.g., RNNs or any other type of deep learning method) to process spectral information 205.

Figure 4:
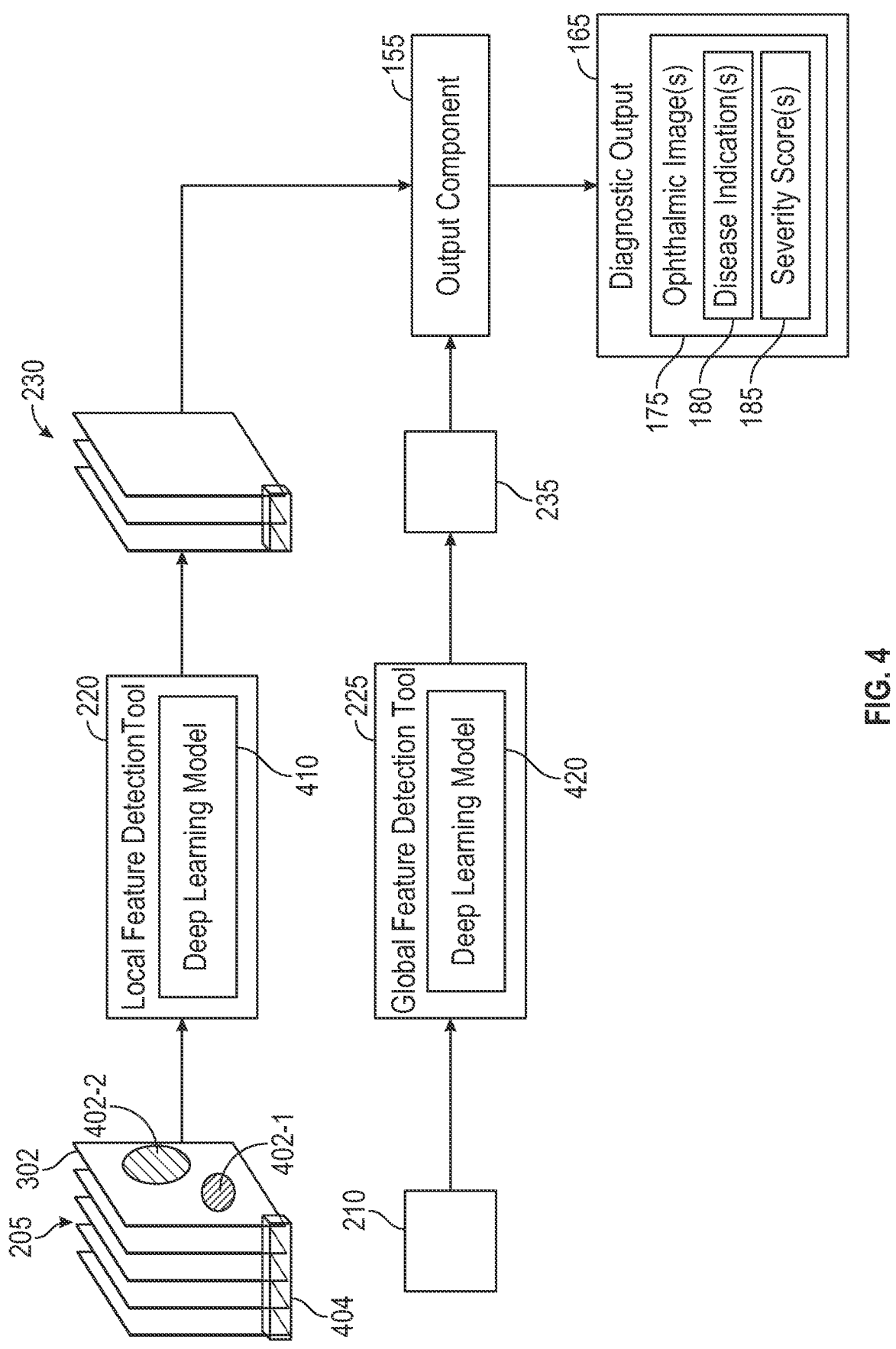
FIG. 4 further illustrates certain components of the workflows illustrated in FIGS. 2A-2B, according to certain embodiments.

FIG. 4 further illustrates certain components of the diagnostic tool 135, described relative to FIGS. 2A-2B, according to certain embodiments. As shown, the spectral information 205 (input into the local feature detection tool 220) includes depth information 404 and multiple spectral features 402 1-2. In certain embodiments, the local feature detection tool 220 uses the deep learning model 410 to extract one or more local features 230 from the spectral information 205. Each local feature 230 includes a spectral feature 402 from a local area (e.g., a single image pixel).

The deep learning model 410 may perform an embedding operation to map the spectral information to an internal representation used for describing (or labeling) ocular diseases. For example, the deep learning model 410 may be trained on a set of spectral features, which are labeled using disease or function labels. The deep learning model 410 may predict the classification labels associated with the local features 230. In certain embodiments, the deep learning model 410 is an RNN. An exemplary RNN is bidirectional long short-term memory (bidirectional LSTM); however, note that the prediction tool 430 may use other neural networks consistent with the functionality described herein.

As also shown in FIG. 4, the global feature detection tool 225 receives spatial information 210 and uses a deep learning model 420 to extract the global features 235. In certain embodiments, the global features 235 includes a set of spectrally encoded spatial information. In certain embodiments, the deep learning model 420 is an RNN. Note, however, that the deep learning model 420 can be any type of deep learning model.

The output component 155 generates the diagnostic output 165 based on the local features 230 and global features 235. In certain embodiments, the output component 155 may use the labels corresponding to the local features 230 to establish "words" to describe the spectral data. For example, each "word" may associate a label (corresponding to a local feature 230) with a description of a retinal disease symptom (e.g., seeing flashes of light, blurry vision, reduced central or peripheral vision, sudden loss of vision, change in color perception) or a particular retinal disease (e.g., retinal tear, retinal detachment, diabetic retinopathy, macular hole, etc.). The output component 155 may then use the global features 235 to combine the "words" into one or more "sentences," which can be used to evaluate a disease pattern or perform early detection. For example, the global features 235 may be used to determine that a group of "words" (that collectively indicate a set of retinal disease symptoms) is indicative of a disease diagnosis, which includes at least one of: (i) a particular retinal disease or (ii) a severity of the retinal disease. Additionally or alternatively, in certain embodiments, the output component 155 can use a neural network (e.g., 2D or 3D CNN) or a vision transformer to generate a probability map of disease onset, based on the local features 230 and global features 235. In an exemplary embodiment, the output component 155 can segment choroidal neovascularization structures from the retinal image to indicate the presence of age related macular degeneration.

FIG. 5 is a flowchart of an example method 500 for analyzing multiple spectral information to generate ophthalmic information, according to certain embodiments. The method 500 may be performed by a diagnostic tool (e.g., diagnostic tool 135).

Method 500 enters at block 505, where the diagnostic tool receives multiple spectral information (e.g., input data 110) associated with a patient's eye. In certain embodiments, the multiple spectral information includes MSI data (e.g., MSI data 105). In certain embodiments, the multiple spectral information includes HSI data (e.g., HSI data 115).

At block 510, the diagnostic tool extracts spectral information (e.g., spectral information 205) from the multiple spectral information and spatial information (e.g., spatial information 210) from the multiple spectral information. In certain embodiments, the diagnostic tool performs dimensionality reduction to extract the spatial information from the multiple spectral information.

At block 515, the diagnostic tool generates a diagnostic output (e.g., diagnostic output 165) associated with the patient's eye, based on evaluating the spectral information and the spatial information with different deep learning models. In certain embodiments, the diagnostic tool uses a first deep learning model to extract a set of local features (e.g., local features 230) from the spectral information and uses a second deep learning model to extract a set of global features (e.g., global features 235) from the spatial information.

The diagnostic tool may group the set of local features and the set of global features to obtain the diagnostic output. In certain embodiments, the diagnostic output includes one or more ophthalmic images (e.g., ophthalmic image(s) 175). Each ophthalmic image may include a disease indication (e.g., disease indication 180). For example, the disease indication may be in the form of one or more segmented regions within the ophthalmic image associated with an ocular disease. The ophthalmic image may also be associated with a severity score (e.g., severity score 185) that identifies a particular ocular disease along with an indication of the severity of the ocular disease.

At block 520, the diagnostic tool sends an indication of ophthalmic information (e.g., ophthalmic information) to a user (e.g., clinician). The ophthalmic information may include at least the diagnostic output.

Although not shown in FIG. 5, in certain embodiments, the method 500 includes generating, by the diagnostic tool, a visualization of the multiple spectral information based on the spectral information. In certain embodiments, the visualization includes a single interpretative image (e.g., interpretative image 125) with one or more features from across one or more spectral bands of the spectral information. In certain embodiments, the diagnostic tool generates the visualization of the multiple spectral information further based on diagnostic criteria (e.g., diagnostic criteria 195) received from a user (e.g., a clinician) via a computing system (e.g., computing system 190). In certain embodiments, the ophthalmic information that is sent to the user (at block 520) also includes the visualization of the multiple spectral information.

Figure 6A:
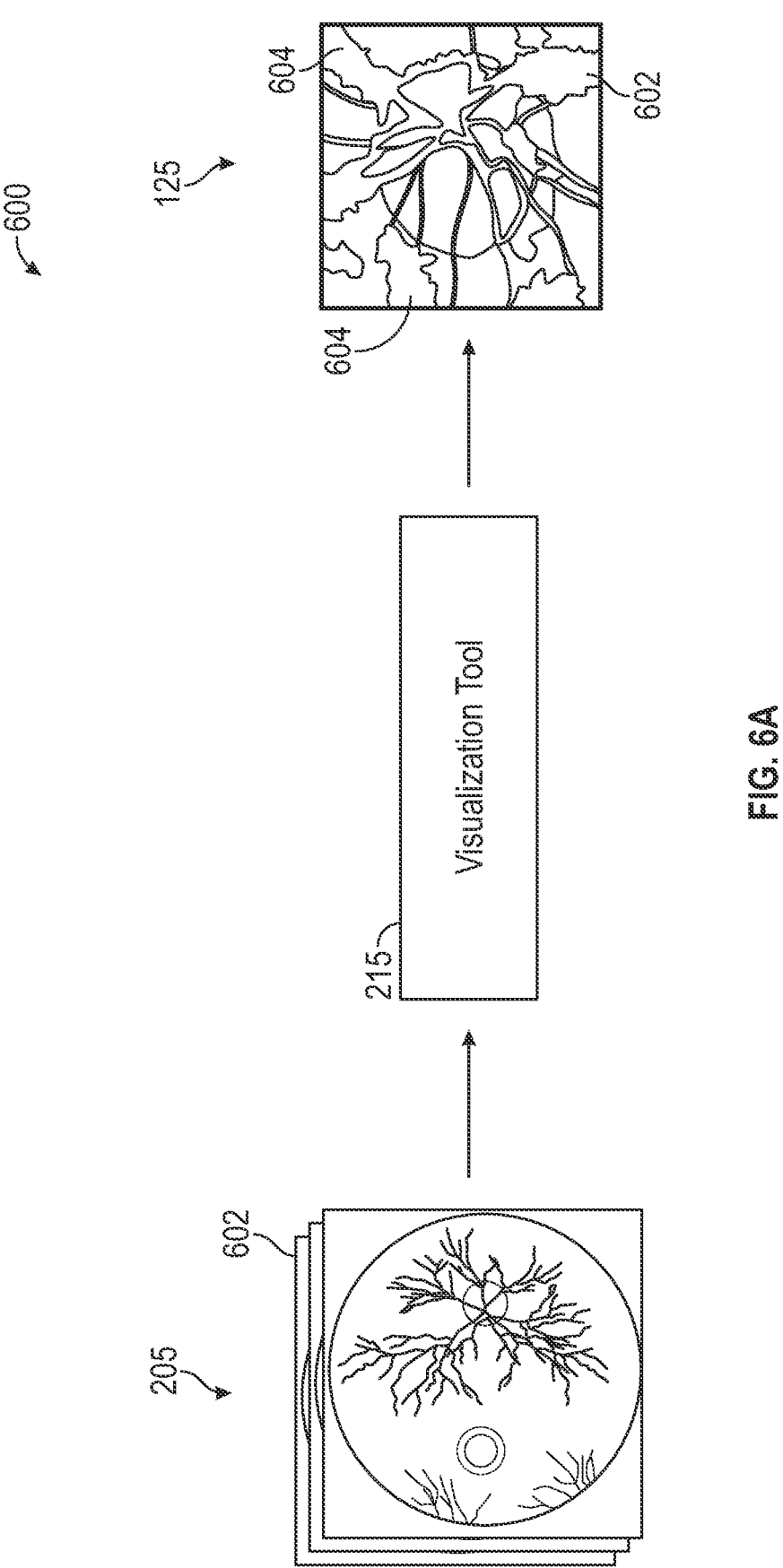
FIGS. 6A-6B illustrates an example scenario for analyzing multiple spectral information to generate ophthalmic information, according to certain embodiments.
Figure 6B:
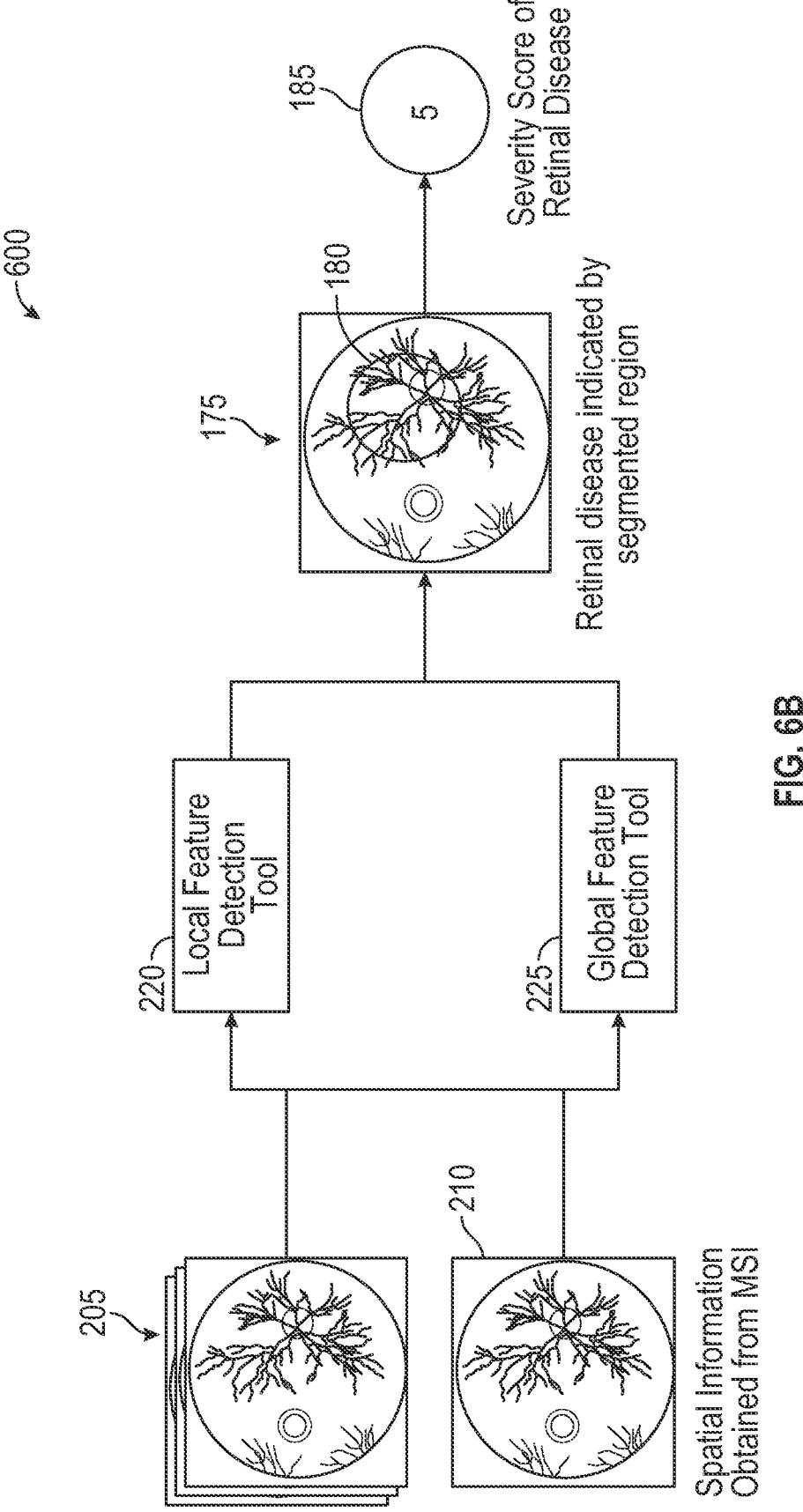

FIGS. 6A-6B illustrate an example sequence 600 of analyzing multiple spectral information to generate ophthalmic information, according to certain embodiments. As shown in FIG. 6A, the visualization tool 215 evaluates the spectral information 205, which includes multiple spectral frames 602, in order to generate the interpretative image 125. As shown, the interpretative image 125 is a single image, which includes one or more (superimposed) features 604 from across the spectral frames 602.

As shown in FIG. 6B, the output from the local feature detection tool 220 and the output from the global feature detection tool 225 is used to generate the ophthalmic image 175 with a disease indication 180. In the depicted embodiment, the disease indication 180 is a segmented region of a retinal disease (e.g., "hard exudates" caused by diabetic macular edema), and has a severity score of "5."

Figure 7:
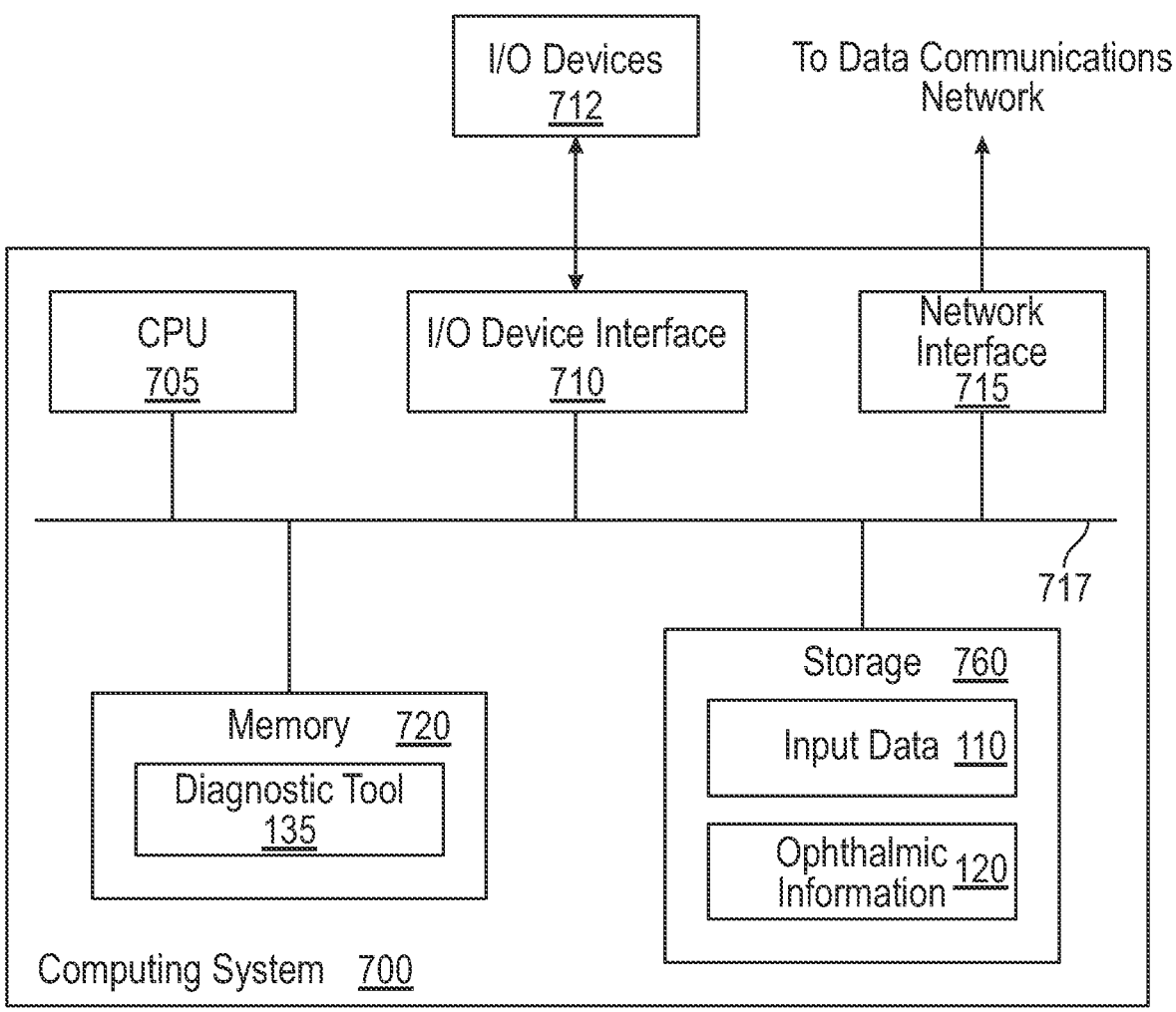
FIG. 7 illustrates an example computing system for analyzing multiple spectral information to generate ophthalmic information, according to certain embodiments.

FIG. 7 illustrates an example computing system 700 configured to automatically initialize an image guided surgery, according to certain embodiments. As shown, the computing system 700 includes, without limitation, a processing unit 705, a network interface 715, a memory 720, and storage 760, each connected to a bus 717. The computing system 700 may also include an I/O device interface 710 connecting I/O devices 712 (e.g., keyboard, display and mouse devices) to the computing system 700. The computing system 700 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used.

The processing unit 705 can include one or more central processing units (CPUs) and/or one or more graphics processing units (GPUs). The processing unit 705 retrieves and executes programming instructions stored in the memory 720 as well as stored in the storage 760. The bus 717 is used to transmit programming instructions and application data between the processing unit 705, I/O device interface 710, storage 760, network interface 715, and memory 720. Note, processing unit 705 is included to be representative of a single CPU, multiple CPUs, a single CPU having multiple processing cores, a single GPU, multiple GPUs, a single GPU having multiple processing cores, or any combination thereof. The memory 720 is generally included to be representative of a random access memory. The storage 760 may be a disk drive or flash storage device. Although shown as a single unit, the storage 760 may be a combination of fixed and/or removable storage devices, such as fixed disc drives, removable memory cards, optical storage, network attached storage (NAS), or a storage area-network (SAN). Illustratively, the memory 720 includes the diagnostic tool 135, which is discussed in greater detail above. Further, storage 760 includes input data 110 and ophthalmic information 120, described above.

In summary, certain embodiments of the present disclosure provide a framework for applying image analytics and AI/ML techniques to automatically process and present clinically relevant information from data acquired using MSI/HSI technology. The framework described herein can be used for various ophthalmic applications, including disease detection, and can overcome challenges in interpreting, visualizing, and utilizing MSI/HSI information.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. An ophthalmic system comprising:
an imaging system adapted to capture multiple spectral information associated with an eye of a patient;
a display;
a memory comprising executable instructions; and
a processor in data communication with the memory and configured to execute the executable instructions to:
extract a first set of information from the multiple spectral information and a second set of information from the multiple spectral information, wherein the first set of information comprises spectral information and the second set of information comprises spatial information;
generate a set of ophthalmic information associated with the eye of the patient, based on evaluating the first set of information with a first deep learning model and the second set of information with a second deep learning model;
generate a visualization of the multiple spectral information based on evaluating the first set of information with a third deep learning model; and
present an indication of the set of ophthalmic information to a user and the visualization to the user via the display.

2. The ophthalmic system of claim 1, wherein the multiple spectral information comprises multispectral imaging (MSI) data.

3. The ophthalmic system of claim 1, wherein the multiple spectral information comprises hyperspectral imaging (HSI) data.

4. The ophthalmic system of claim 1, wherein the processor is configured to execute the executable instructions to extract the second set of information by performing a dimensionality reduction operation on the multiple spectral information.

5. The ophthalmic system of claim 1, wherein:
the multiple spectral information comprises a plurality of images, each image associated with a different spectral band; and
the visualization comprises a single image comprising a plurality of features from one or more of the plurality of images.

6. The ophthalmic system of claim 1, wherein:
the multiple spectral information comprises a plurality of images, each image associated with a different spectral band; and
the processor is configured to execute the executable instructions to generate the set of ophthalmic information by (i) extracting, via the first deep learning model, a first set of features from one or more regions of one or more of the plurality of images and (ii) extracting, via the second deep learning model, a second set of features from the spatial information.

7. The ophthalmic system of claim 6, wherein:
the first set of features comprises a set of local features;
each of the one or more regions comprises a single pixel from one of the plurality of images; and
the second set of features comprises a set of global features.

8. The ophthalmic system of claim 6, wherein the set of ophthalmic information comprises a prediction of a condition associated with the eye of the patient.

9. The ophthalmic system of claim 8, wherein the prediction comprises (i) an ophthalmic image comprising one or more segmented regions associated with the condition and (ii) a score indicating a severity of the condition.

10. A computer-implemented method comprising:

receiving multiple spectral information associated with an eye of a patient;

extracting a first set of information from the multiple spectral information and a second set of information from the multiple spectral information, wherein the first set of information comprises spectral information and the second set of information comprises spatial information;

generating a set of ophthalmic information associated with the eye of the patient, based on evaluating the first set of information with a first deep learning model and the second set of information with a second deep learning model;

generating a visualization of the multiple spectral information based on evaluating the first set of information with a third deep learning model; and presenting an indication of the set of ophthalmic information to a user and the visualization to the user via a display.

11. The computer-implemented method of claim 10, wherein the multiple spectral information comprises multi-spectral imaging (MSI) data.

12. The computer-implemented method of claim 10, wherein the multiple spectral information comprises hyper-spectral imaging (HSI) data.

13. The computer-implemented method of claim 10, wherein extracting the second set of information comprises performing a dimensionality reduction operation on the multiple spectral information.

14. The computer-implemented method of claim 10, wherein:

the multiple spectral information comprises a plurality of images, each image associated with a different spectral band; and the visualization comprises a single image comprising a plurality of features from one or more of the plurality of images.

15. The computer-implemented method of claim 10, wherein:

the multiple spectral information comprises a plurality of images, each image associated with a different spectral band; and generating the set of ophthalmic information comprises (i) extracting, via the first deep learning model, a first set of features from one or more regions of one or more of the plurality of images and (ii) extracting, via the second deep learning model, a second set of features from the spatial information.

16. The computer-implemented method of claim 15, wherein:

the first set of features comprises a set of local features;

each of the one or more regions comprises a single pixel from one of the plurality of images; and the second set of features comprises a set of global features.

17. The computer-implemented method of claim 15, wherein the set of ophthalmic information comprises a prediction of a condition associated with the eye of the patient.

18. A non-transitory computer-readable medium having computer executable instructions stored thereon, the computer executable instructions being executable by one or more processors to cause a system to perform operations, the operations comprising:

receiving multiple spectral information associated with an eye of a patient;

extracting a first set of information from the multiple spectral information and a second set of information from the multiple spectral information, wherein the first set of information comprises spectral information and the second set of information comprises spatial information;

generating a set of ophthalmic information associated with the eye of the patient, based on evaluating the first set of information with a first deep learning model and the second set of information with a second deep learning model;

generating a visualization of the multiple spectral information based on evaluating the first set of information with a third deep learning model; and presenting an indication of the set of ophthalmic information to a user and the visualization to the user via a display.

* * * * *